United States Patent
Shen et al.

(10) Patent No.: US 10,022,407 B2
(45) Date of Patent: Jul. 17, 2018

(54) **USE OF A *LACTOBACILLUS RHAMNOSUS* STRAIN FOR REDUCING WEIGHT GAIN AND/OR INSULIN RESISTANCE**

(71) Applicants: COMPAGNIE GERVAIS DANONE, Paris (FR); TUFTS UNIVERSITY, Boston, MA (US)

(72) Inventors: Jian Shen, Shanghai (CN); Jingjing Wang, Shanghai (CN); Liping Zhao, Shanghai (CN); Martin Saul Obin, West Newton, MA (US); Muriel Derrien, Bures sur Yvette (FR); Emilie Rocher, Massy (FR); Johan Van Hylckama Vlieg, Marly le Roi (FR)

(73) Assignees: Compagnie Gervais Danone, Paris (FR); Tufts University, Boston, MA (US)

( * ) Notice: Subject to any disclaimer, the term of this patent is extended or adjusted under 35 U.S.C. 154(b) by 45 days.

(21) Appl. No.: 14/442,040

(22) PCT Filed: Nov. 12, 2012

(86) PCT No.: PCT/CN2012/084462
§ 371 (c)(1),
(2) Date: May 11, 2015

(87) PCT Pub. No.: WO2014/071633
PCT Pub. Date: May 15, 2014

(65) Prior Publication Data
US 2015/0297646 A1 Oct. 22, 2015

(51) Int. Cl.
| | | |
|---|---|---|
| *A61K 35/742* | (2015.01) | |
| *C12N 1/20* | (2006.01) | |
| *A61K 35/747* | (2015.01) | |
| *C12R 1/225* | (2006.01) | |
| *A23L 33/135* | (2016.01) | |

(52) U.S. Cl.
CPC .......... *A61K 35/742* (2013.01); *A23L 33/135* (2016.08); *A61K 35/747* (2013.01); *C12N 1/20* (2013.01); *C12R 1/225* (2013.01); *A23V 2002/00* (2013.01); *A23Y 2220/73* (2013.01)

(58) Field of Classification Search
None
See application file for complete search history.

(56) References Cited

U.S. PATENT DOCUMENTS

| | | |
|---|---|---|
| 2005/0186189 A1 | 8/2005 | Hsu et al. |
| 2010/0216212 A1 | 8/2010 | Morita et al. |
| 2011/0059058 A1* | 3/2011 | Chambaud .......... A23C 9/1234 424/93.45 |
| 2012/0114622 A1 | 5/2012 | Darimont et al. |

FOREIGN PATENT DOCUMENTS

| | | | |
|---|---|---|---|
| CN | 101410128 A | * | 4/2009 |
| CN | 102215848 A | | 10/2011 |
| CN | 102225078 A | | 10/2011 |
| EP | 2 216 035 A1 | | 11/2010 |
| EP | 2 216 036 A1 | | 11/2010 |

OTHER PUBLICATIONS

Caropreso et al., Lactobacillus Rhamnosus GG treatment: A promising tool for improving hypertransaminasemia of obese children, Abstracts/Digestive and Liver Disease 38 (2006) A87-A120.*
International Search Report and Written Opinion issued in corresponding International Patent Application No. PCT/CN2012/084462 dated Aug. 22, 2013.
Lee et al. (2006) Human originated bacterial, Lactobacillus rhamnosus PL60, produce conjugated linoleic acid and show anti-obesity effects in diet-induced obese mice, Biochim. Biophys. Acta, 1761:736-744.
Tabuchi et al. (2005) Effect of administration of Lactobacillus rhamnosus GG on postprandial blood glucose levels in rats, Milk Science, 54:17-21.

* cited by examiner

*Primary Examiner* — Suzanne M Noakes
*Assistant Examiner* — Stephen M Chong
(74) *Attorney, Agent, or Firm* — Morgan, Lewis & Bockius LLP

(57) ABSTRACT

Provided are the use of *Lactobacillus rhamnosus* strain CNCM I-3690 for reducing diet-induced weight gain and/or diet-induced insulin resistance, and treating disorders resulting therefrom, such as overweight, obesity and obesity-related disorders in a subject.

3 Claims, 5 Drawing Sheets

Figure 1:
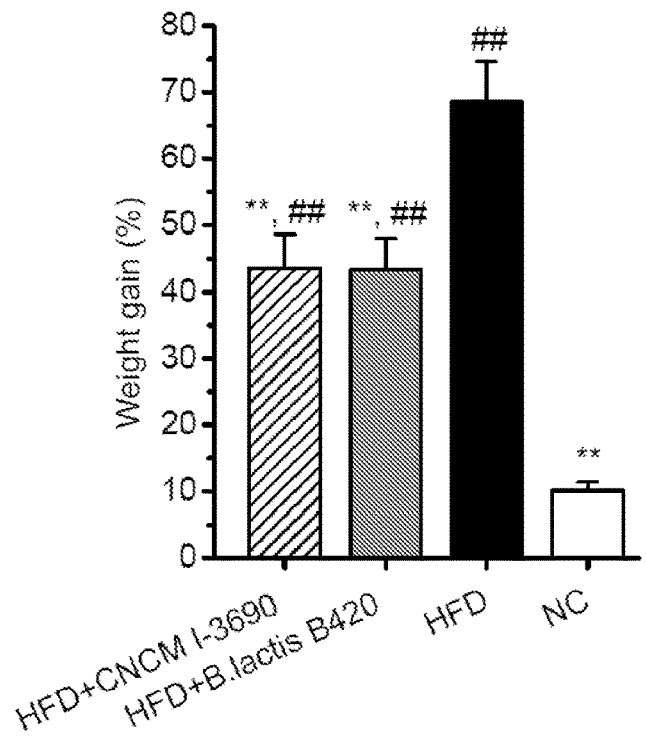
Figure 1:
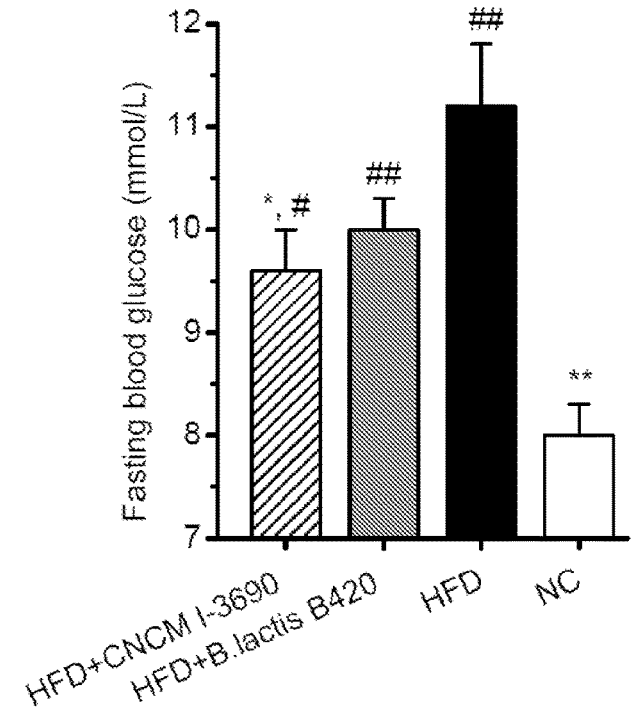
Figure 1:
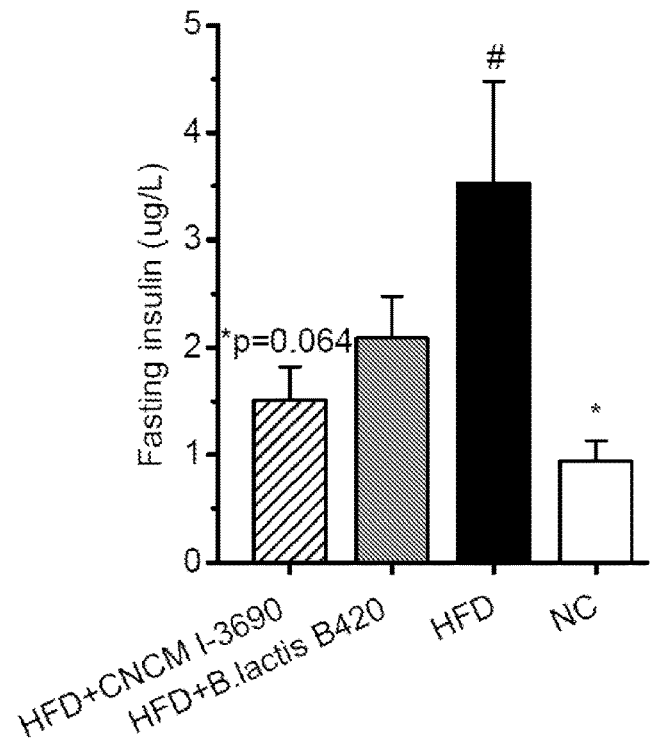
Figure 1:
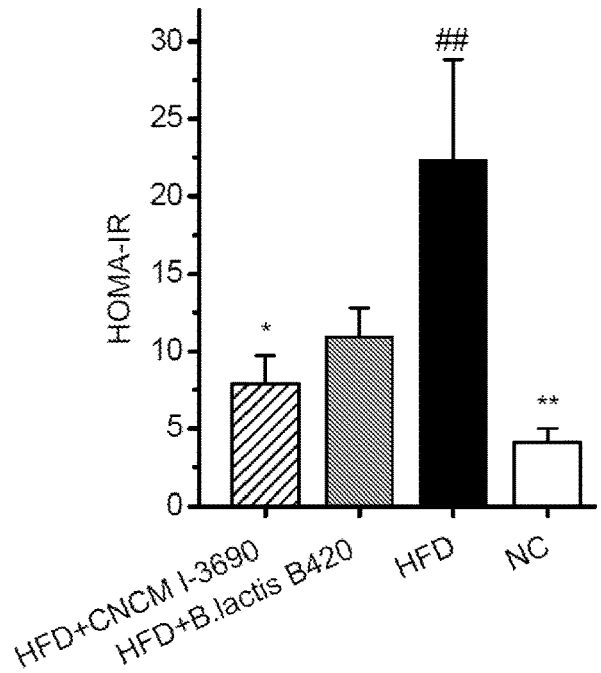
Figure 1:
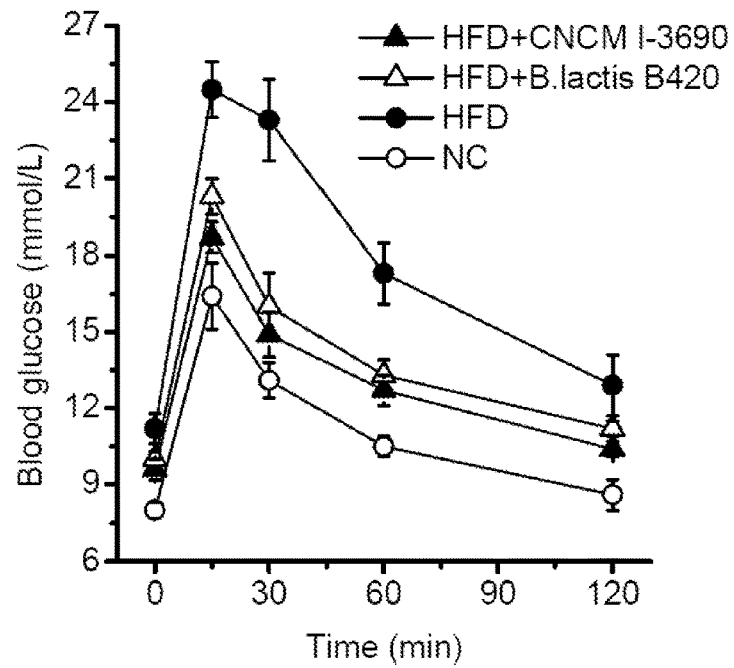
Figure 1:
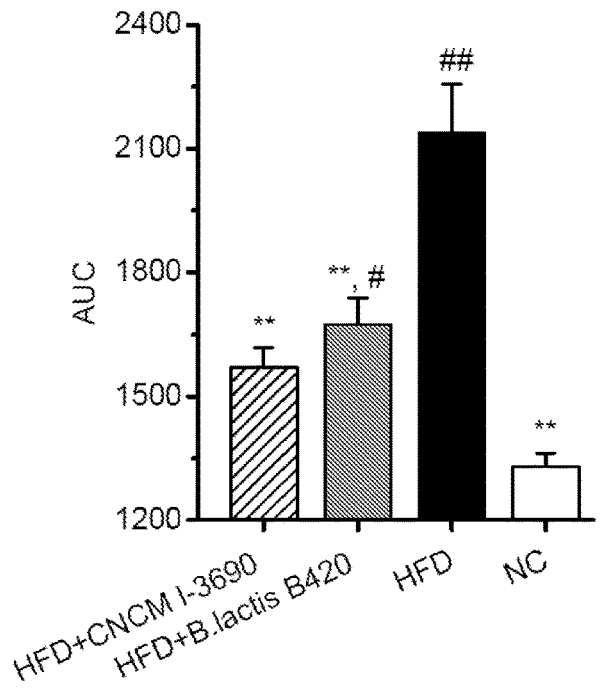

USE OF A *LACTOBACILLUS RHAMNOSUS* STRAIN FOR REDUCING WEIGHT GAIN AND/OR INSULIN RESISTANCE

The invention relates to the field of probiotics, and more specifically to their use for regulating weight gain and insulin resistance.

The prevalence of overweight and obesity has considerably increased in many parts of the world over the past 25 years. A body mass index (BMI) greater than or equal to 25 is considered overweight and a BMI greater or equal to 30 is defined as obesity. The number of obese people worldwide has more than doubled since 1980. In 2008, more than 1.4 billion adults, 20 and older, were overweight. Of these over 200 million men and nearly 300 million women were obese.

Obesity is often associated with insulin resistance (i.e. a condition where cells are no longer able to respond adequately to insulin) leading to major diseases that englobe metabolic syndrome such as hypertension, type II diabetes, cardiovascular diseases, as well as liver diseases.

Although differences in fat accumulation and body weight among individuals may be correlated with various factors, such as genetic background, health conditions, medical treatments, or age, it is generally acknowledged that one of the primary causes of the current frequency of obesity and insulin resistance is the combination of reduced physical activity in the daily lives, with the western-style diet, rich in high-fat and high-sucrose foods.

Also, numerous investigations in recent years have shown that obesity and obesity-related metabolic disorders are associated with changes in the composition of the intestinal microbiota (for review see LEY, Curr Opin Gastroenterol. 26, 5-11, 2010) and that gut microbiota can impact host metabolism and increase energy harvest from the diet (MARIK, Front Endocrinol (Lausanne), 3, 87, 2012).

Therefore, it has been suggested that modulation of gut microbiota is a target for improving metabolic syndrome. This can be achieved by using prebiotics, probiotics, or synbiotics, that may help to reduce obesity and obesity-related metabolic disorders, including insulin resistance (MALLAPPA et al., Indian J Endocrinol Metab, 16, 20-7, 2012; DELZENNE et al., Nat Rev Endocrinol, 7, 639-46, 2011).

Some probiotic strains have been reported to decrease fat accumulation and/or obesity-related metabolic disorders. LEE et al. (Biochim Biophys Acta, 1761, 736-44, 2006) have shown that *Lactobacillus rhamnosus* strain PL60, which produces conjugated linoleic acid has anti-obesity effects in diet-induced obese mice; *Lactobacillus gasseri* SBT2055 has been shown to reduce abdominal adiposity and body weight in human adults (KADOOKA et al., Eur J Clin Nutr, 64, 636-43, 2010), and *Lactobacillus gasseri* BNR17 has been shown to reduce the gain in body weight in rats fed a high-carbohydrate diet (KANG et al., J Microbiol, 48, 712-4, 2010). ANDREASEN et al. (Br J Nutr, 104, 1831-8, 2010) reported an improvement of insulin resistance upon administration of *Lactobacillus acidophilus* NCFM. *Lactobacillus plantarum* strain No. 14 was shown to reduce adipocyte size in mice fed high-fat diet (TAKEMURA et al., Exp Biol Med (Maywood), 235, 849-56, 2010). ARONSSON et al. (PLoS One, 5, 2010) reported that *Lactobacillus paracasei* ssp *paracasei* strain F19 can decrease fat storage by increasing the expression of angiopoietin-like 4 protein (ANGPTL4). MA et al. (J Hepatol, 49, 821-30, 2008) reported that probiotics VSL#3 improve high fat diet-induced hepatic steatosis and insulin resistance by increasing hepatic NKT cells. Modulation of the murine microbiome by *Lactobacillus rhamnosus* GG and *Lactobacillus sakei* NR28, with a concomitant anti-obesity effect, was reported by JI et al. (Benef Microbes, 3, 13-22, 2012). AN et al. (Lipids Health Dis, 10, 116, 2011) described the antiobesity and lipid-lowering effects of a mixture of Bifidobacterial strains (*B. pseudocatenulatum* SPM 1204, *B. longum* SPM 1205, and *B. longum* SPM 1207) in high fat diet-induced obese rats. PCT application WO2007/043933 proposes the use of *Lactobacillus casei* F19, *Lactobacillus acidophilus* NCFB 1748 or *Bifidobacterium lactis* Bb12 for reducing food intake and fat deposition, and preventing or treating obesity and insulin insensitivity. AMAR et al. (AMAR et al., EMBO Mol Med, 3, 559-72, 2011) showed that administration of the probiotic strain *Bifidobacterium lactis* B420 to diabetic mice improved the fasting glycaemia and restored the glucose turnover rate to the level of the control mice fed with normal chow.

The effects of these different probiotics are strain-specific, and appear to be mediated by different mechanisms. Thus, a need remains for other probiotic strains that can be used for controlling the development of overweight and obesity and metabolic diseases associated therewith.

The inventors have undertaken to study the preventive effects of probiotics on diet-induced obesity and insulin resistance in mice. They have found that orally administrated *Lactobacillus rhamnosus* strain CNCM 1-3690 to high fat diet (HFD)-fed mice at $10^8$ cells/day for 12 weeks, significantly reduced body weight gain, insulin resistance. Further, analysis of gut microbiota by 454 pyrosequencing of 16S rRNA gene showed that *Lactobacillus rhamnosus* strain CNCM 1-3690 changed the structure of gut microbiota compared to HF diet. More detailed analysis revealed that strain CNCM 1-3690 changed the relative abundance of different operational taxonomic units (OTUs), but most elevated OTUs were from lactate and acetate-producing bacteria. Short chain fatty acid analysis of cecal content confirmed that strain CNCM 1-3690 significantly increased the amount of intestinal acetate compared to HFD, in agreement with microbiota analysis by 454 pyrosequencing.

Strain CNCM 1-3690 was deposited according to the Budapest Treaty at the CNCM on Nov. 19, 2006. It is disclosed in PCT application WO 2009/122042, which reports its anti-microbial and immunomodulatory properties. This strain has also anti-oxidant properties, which are described in PCT application WO 2011/083354.

Therefore, an object of the present invention is the use of Lactobacillus rhamnosus strain CNCM 1-3690, or of a composition containing said strain, for reducing diet-induced weight gain and/or diet-induced insulin resistance in a subject.

"Diet induced weight gain" and "diet-induced insulin resistance" are defined herein as weight gain and insulin resistance resulting from an excessive dietary intake of fat (in particular unsaturated fat) and/or simple sugars, including in particular sucrose and fructose. For a given subject, an excessive intake of dietary fat and/or simple sugars refers to the consumption of an amount of dietary fat and/or of an amount of simple sugars higher than the amount necessary to meet the physiological needs and maintain the energy balance of said subject. The effect of a treatment on reduction of diet-induced weight gain or insulin resistance in a subject can be assessed by comparing weight gain or insulin resistance observed in a subject receiving the treatment with those observed in the same subject without treatment receiving the same diet and having the same level of physical activity.

Tests for evaluating insulin resistance in a subject are known in the art (for review see for instance FERRANNINI & MARI, J Hypertens., 16, 895-906, 1998). The level of insulin resistance in a subject can be measured with any insulin resistance test known in the art, such as the homeostatic model assessment of insulin resistance (HOM-IR).

The present invention also encompasses *Lactobacillus rhamnosus* strain CNCM I-3690 or a composition containing said strain, for use in the treatment, prevention, or alleviation of a condition resulting from diet-induced weight gain and/or diet-induced insulin resistance.

Examples of conditions resulting from diet-induced weight gain and/or diet-induced insulin resistance are overweight, obesity, and related disorders, such as type 2 diabetes, non-alcoholic fatty liver disease (NAFLD), hypertension, etc.

The present invention also provides a method for reducing diet-induced weight gain and/or diet-induced insulin resistance in a subject in need thereof, wherein said method comprises administrating to said subject *Lactobacillus rhamnosus* strain CNCM 1-3690, or a composition containing said strain.

*Lactobacillus rhamnosus* strain CNCM 1-3690 can be used in the form of whole bacteria which may be living or not. Alternatively, it can be used in the form of a bacterial lysate or in the form of bacterial fractions.

The compositions for use in the present invention can be in any form suitable for administration, in particular oral administration. This includes for instance solids, semi-solids, liquids, and powders. Liquid compositions are generally preferred for easier administration, for instance as drinks When the bacteria are in the form of living bacteria, the composition may typically comprise $10^5$ to $10^{13}$ colony forming units (cfu), preferably at least $10^6$ cfu, more preferably at least $10^7$ cfu, still more preferably at least $10^8$ cfu, and most preferably at least $10^9$ cfu per g dry weight of the composition. In the case of a liquid composition, this corresponds generally to $10^4$ to $10^{12}$ colony forming units (cfu), preferably at least $10^5$ cfu, more preferably at least $10^6$ cfu, still more preferably at least $10^7$ cfu, and most preferably at least $10^9$ cfu/ml.

Preferred compositions for use in the present invention are nutritional compositions, including food products and in particular dairy products. These nutritional compositions also include food supplements, and functional food. A "food supplement" designates a product made from compounds usually used in foodstuffs, but which is in the form of tablets, powder, capsules, potion or any other form usually not associated with aliments, and which has beneficial effects for one's health. A "functional food" is an aliment which also has beneficial effects for one's health. In particular, food supplements and functional food can have a physiological effect—protective or curative—against a disease, for example against a chronic disease.

Other examples of compositions suitable for use in the present invention are pharmaceutical compositions.

The compositions of the invention can also comprise, besides strain CNCM 1-3690 one or more other strain(s) of lactic acid bacteria, probiotic or not, for instance one or more bacterial strain(s) selected from the genera *Lactobacillus, Lactococcus, Streptococcus*, and *Bifidobacteria*. In particular, this (these) other strain(s) can include one or more strain(s) of *Streptococcus thermophilus*, and/or one or more strains(s) of *Lactobacillus bulgaricus*.

The present invention will be understood more clearly from the further description which follows, which refers to an example illustrating the effect of the bacterial strain CNCM 1-3690 on lipid storage.

FIGURE LEGENDS

FIG. 1: Weight gain (A), fasting blood glucose (B), fasting insulin (C), HOMA-IR (D), OGTT (E) and areas under the curve (AUC) of OGTT (F) for four groups: NC, HFD, HFD+CNCM I-3690, HFD+*B. lactis* B420 (Danisco). Data are shown as means ±S.E.M. **p<0.01, *p<0.05 when compared to HFD group, and ##p<0.01, #p<0.05 when compared to NC group by One Way-ANOVA followed by Tukey post hoc test in SPSS. HOMA-IR is calculated according to the following formula: fasting blood glucose (mmol/L)×fasting insulin (mU/L)/22.5.

Figure 2:
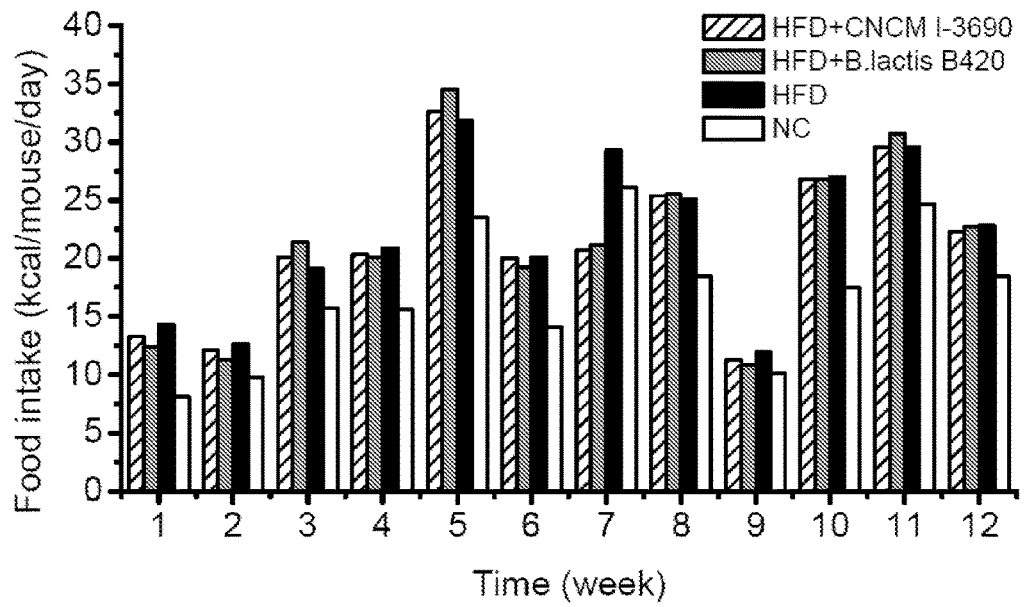

FIG. 2: Food intake of four groups each week. Data are shown as means of two cages of mice, so no statistical analysis was performed.

Figure 3:
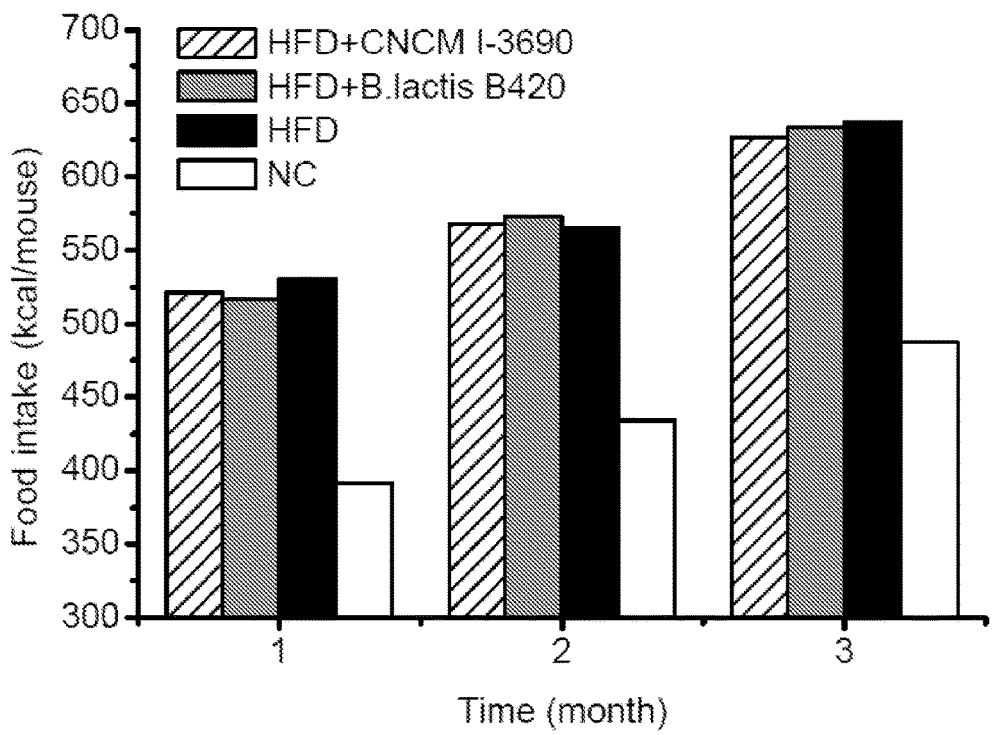

FIG. 3: Cumulative food intake of four groups in each month of the animal trial. Data are shown as means of two cages of mice, so no statistical analysis was performed.

Figure 4:
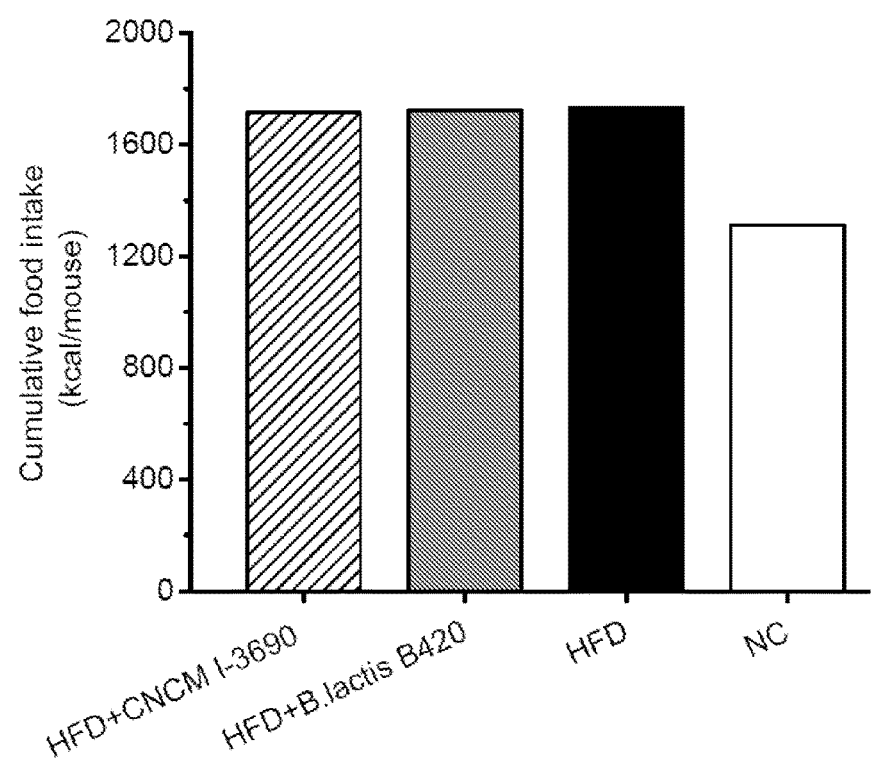

FIG. 4: Cumulative food intake of four groups during 12 weeks. Data are shown as means of two cages of mice, so no statistical analysis was performed.

EXAMPLE 1

Improvement of High Fat Diet-Induced Obesity and Insulin Resistance By *L. Rhamnosus* CNCM 1-3690.

Materials and Methods

C57BL/6J mice (male, at age 12 weeks) were divided into 3 groups (8 mice per group) under different treatments as follows:

Group A: high fat diet, containing 34.9% fat, 5.24 kcal/g, from Research Diets, Inc., New Brunswick, N.J. (HFD);

Group B: high fat diet, plus probiotic strain *L. rhamnosus* CNCM 1-3690, at $10^8$ CFU/mouse/day (HFD+CNCM 1-3690);

Group C: high fat diet, plus probiotic strain *Bifidobacterium lactis* B420 (Danisco), at $10^8$ CFU/mouse/day (HFD+*B. lactis* B420), previously reported to reduce adverse effects on metabolism associated with high-fat diet (AMAR et al., 2011, cited above), as a comparison;

Group D; Normal chow, containing 4.3% fat, 3.85 kcal/g, from Research Diets, Inc., New Brunswick, N.J. (NC).

*L. rhamnosus* CNCM 1-3690 or *Bifidobacterium lactis* B420 suspension were prepared before the animal trial, stored at −80° C. and thawed 1 hour before they were administered to each mouse by oral feeding.

Animal treatments lasted for 12 weeks, during which the body weight of each mouse and food intake of every cage of mice were measured twice a week. Fresh stool and urine samples were collected once a month by using a metabolic cage and immediately stored at −80° C. for subsequent analysis.

The amount of the probiotic strains in the feces of mice at 2nd, 6th and 11th weeks during the probiotic administration was quantified by reverse transcription (RT)-qPCR, and the results confirmed that they could survive in the intestine.

At the end of the trial, after 5 h of food deprivation, blood was collected from the orbital plexus, and serum was isolated by centrifugation at 3000 rpm at 4° C. for 15 min. All animals were sacrificed by cervical dislocation. Epididymal fat pads, liver and jejunum were excised, weighed, and immediately kept in RNALater (Ambion) after sacrifice.

Oral glucose tolerance tests (OGTT) were performed before the sacrifice of animals. After 5 h of food deprivation, 2.0 g/kg body weight glucose was administered orally to the mice. Blood samples were taken from the tail to measure blood glucose levels before and 15, 30, 60, and 120 min after glucose administration by using an ACCU-Check glucose meter (Roche Diagnostics, Canada). The blood glucose level before glucose administration is regarded as fasting blood glucose (FBG) level. Fasting insulin (FINS) level was determined by ELISA assay (Mercodia, Sweden). HOMA-IR was calculated according to the following formula: fasting blood glucose (mmol/L)×fasting insulin (mU/L)/22.5.

Results

The results are shown in FIG. 1: A: Body weight gain; B: Fasting blood glucose levels (FBG); C: Fasting insulin levels (FINS); D: homeostasis assessment of insulin resistance (HOMA-IR) index; E: Curve of Oral Glucose Tolerance Test (OGTT), F: Areas under the curve (AUC) of OGTT. Data are shown as means ±S.E.M. **$p<0.01$, *$p<0.05$ when compared to HFD group, and ##$p<0.01$, #$p<0.05$ when compared to NC group by One Way-ANOVA followed by Tukey post hoc test in SPSS.

Compared with NC-fed mice, the HFD group showed higher weight gain (FIG. 1A), elevated levels of fasting blood glucose (FIG. 1B), of fasting insulin (FIG. 1C), and of HOMA-IR (FIG. 1D), as well as decreased glucose tolerance (FIG. 1E, F). The supplement of two probiotic strains to HFD feeding significantly decreased the body weight gain (FIG. 1A). Although there was no significant difference in Fasting Blood glucode (FBG) and Fasting insulin (FINS) levels between HFD+probiotics groups and HFD group both *L. rhamnosus* CNCM 1-3690 or *Bifidobacterium lactis* B420 reduced the HOMA-IR index, and this reduction was significant in the case of CNCM 1-3690 (FIG. 1D). The two strains also significantly decreased glucose intolerance (FIG. 1E, F), indicating that they could improve insulin resistance.

The average energy intake per mouse per day (FIG. 2) was calculated for each of the twelve weeks of the trial. During all the trial, the energy intake of NC group was the lowest, and the energy intake of HFD+probiotic groups was almost the same with that of the HFD group except for the 7$^{th}$ week. Moreover, cumulative energy intake of four groups of animal during 3 months (FIG. 3) and cumulative energy intake of four groups of animal during 12 weeks (FIG. 4) were calculated. This indicates that the body weight reduction observed for the probiotic treated groups cannot be attributed to a reduction of the energy intake.

These results show that the two probiotic strains significantly improved the obesity and insulin resistance induced by HFD, and that the improvement provided by *L. rhamnosus* strain CNCM I-3690 is at least comparable to that provided by *Bifidobacterium lactis* B420.

The invention claimed:

1. A method of reducing diet-induced weight gain and/or diet-induced insulin resistance in a subject, comprising administering to a subject in need thereof a fermented food product comprising at least $10^6$ CFU/g of a *Lactobacillus rhamnosus* strain deposited at the Collection Nationale de Cultures de Micro-organismes (CNCM) with accession number I-3690.

2. The method of claim 1, wherein the method is for the treatment, or alleviation of a condition resulting from diet-induced weight gain and/or diet-induced insulin resistance, and said condition is selected from the group consisting of being overweight and obesity.

3. The method of claim 1, wherein said fermented food product is a fermented dairy product.

\* \* \* \* \*